(12) United States Patent
Senden et al.

(10) Patent No.: US 10,729,917 B2
(45) Date of Patent: Aug. 4, 2020

(54) TREATMENT ASSESSMENT DEVICE

(71) Applicant: KONINKLIJKE PHILIPS N.V., Eindhoven (NL)

(72) Inventors: Dave Senden, Eindhoven (NL); Guillaume Leopold Theodorus Frederik Hautvast, Veldhoven (NL); Jacobus Sigbertus Marie Geraats, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 118 days.

(21) Appl. No.: 16/079,185

(22) PCT Filed: Mar. 23, 2017

(86) PCT No.: PCT/EP2017/056983
§ 371 (c)(1),
(2) Date: Aug. 23, 2018

(87) PCT Pub. No.: WO2017/162820
PCT Pub. Date: Sep. 28, 2017

(65) Prior Publication Data
US 2019/0046814 A1   Feb. 14, 2019

(30) Foreign Application Priority Data

Mar. 24, 2016 (EP) ..................... 16162329

(51) Int. Cl.
*A61N 5/10* (2006.01)
*A61B 34/10* (2016.01)
*A61B 18/04* (2006.01)

(52) U.S. Cl.
CPC ............ *A61N 5/1027* (2013.01); *A61B 34/10* (2016.02); *A61N 5/1049* (2013.01); *A61B 18/04* (2013.01);

(Continued)

(58) Field of Classification Search
CPC ..... A61N 5/1027; A61N 5/1049; A61B 34/10
(Continued)

(56) References Cited

U.S. PATENT DOCUMENTS 5,511,549 A   4/1996   Legg et al.
5,638,819 A   6/1997   Manwaring et al.
(Continued)

FOREIGN PATENT DOCUMENTS

JP         2015013069 A      1/2015

OTHER PUBLICATIONS

F.T.S. Yu et al., "Fiber Optic Sensors". Marcel Dekker Inc., chapter 4 (2002).
(Continued)

*Primary Examiner* — John P Lacyk
(74) *Attorney, Agent, or Firm* — Sherry Austin

(57) ABSTRACT

The invention relates to a treatment assessment device (37) for assessing a treatment of a subject, wherein a current treatment is tracked by a tracking unit (15, 30) and previous conformance values being indicative of previous degrees of conformance of previous treatments with previous treatment plans are provided. A visualization unit (34) generates a visualization being indicative of a current degree of conformance of the current treatment with the current treatment plan in relation to the previous degrees of conformance based on the tracking of the current treatment, the current treatment plan and the provided previous conformance values. The visualization can be shown on a display such that a physician can see how well the current treatment conforms to the treatment plan in comparison to the degree of conformance achieved in previous treatments, thereby providing an assessment of the quality of the current treatment in relation to previous treatments.

12 Claims, 11 Drawing Sheets

(52) U.S. Cl.
CPC . *A61B 2034/107* (2016.02); *A61N 2005/1041* (2013.01); *A61N 2005/1074* (2013.01)

(58) Field of Classification Search
USPC ........................................................ 600/1–8
See application file for complete search history.

(56) References Cited

U.S. PATENT DOCUMENTS

| | | |
|---|---|---|
| 8,112,292 B2 | 2/2012 | Simon |
| 9,925,391 B2 | 3/2018 | Carpenter et al. |
| 2006/0293583 A1 | 12/2006 | Saracen et al. |
| 2013/0102891 A1 | 4/2013 | Binnekamp et al. |
| 2015/0216445 A1 | 8/2015 | Carmeli et al. |

OTHER PUBLICATIONS

"A Practical Guide to Quality Control of Brachytherapy Equipment", edited by J. Venselaar and J. Perez Calatayud, European Society for Therapeutic Radiology and Oncology (2004).

Fast M.F. et al., "Assessment of MLC racking performance during hypofractionated prostate radiotherapy using real-time dose reconstruction", Physics in Medicine and Biology, Institute of Physics Publishing, Bristol GB, vol. 61, No. 4, (Jan. 27, 2016), pp. 1546-1562.

TREATMENT ASSESSMENT DEVICE

CROSS-REFERENCE TO PRIOR APPLICATIONS

This application is the U.S. National Phase application under 35 U.S.C. § 371 of International Application Serial No. PCT/EP2017/056983, filed on Mar. 23, 2017, which claims the benefit of European Patent Application No. 16162329.3, filed on Mar. 24, 2016. This application is hereby incorporated by reference herein.

FIELD OF THE INVENTION

The invention relates to a treatment assessment device, method and computer program for assessing a treatment of a subject. The invention relates further to a treatment system for treating a subject, wherein the treatment system comprises the treatment assessment device.

BACKGROUND OF THE INVENTION

A treatment system is, for instance, a high-dose rate (HDR) brachytherapy system. A HDR brachytherapy system comprises a brachytherapy catheter to be introduced into a target region, wherein within the brachytherapy catheter a radioactive radiation source is moved to different dwell positions at which the radioactive radiation source is located for respective dwell times. The target region is treated by radioactive radiation emitted by the radioactive radiation source at the different dwell positions for the respective dwell times.

Before performing the HDR brachytherapy treatment, a treatment plan is generated, wherein the treatment plan includes, for instance, a planned position of the brachytherapy catheter within the subject. While a physician introduces the brachytherapy catheter into the subject, the position of the brachytherapy catheter may be tracked by using an electromagnetic tracking unit and the tracked position of the brachytherapy catheter may be shown together with the planned position of the brachytherapy catheter on a display for guiding the physician. After the physician has introduced the brachytherapy catheter into the subject, there might be a deviation between the current position of the brachytherapy catheter and the planned position of the brachytherapy catheter, i.e. the planned position and the current position may not perfectly match to each other. It is then difficult for the physician to assess whether this deviation and hence a treatment performed by using this positioning of the brachytherapy catheter is good enough, i.e. acceptable, or whether a repositioning is required.

SUMMARY OF THE INVENTION

It is an object of the present invention to provide a treatment assessment device, method and computer program for assessing a treatment of a subject. It is a further object of the present invention to provide a treatment system for treating a subject, which comprises the treatment assessment device.

In a first aspect of the present invention a treatment assessment device for assessing a treatment of a subject is presented, wherein a current treatment is tracked by a tracking unit and the treatment assessment device comprises:

a treatment plan providing unit for providing a current treatment plan, a conformance values providing unit for providing previous conformance values being indicative of previous degrees of conformance of previous treatments with previous treatment plans, and a visualization unit for generating a visualization being indicative of a current degree of conformance of the current treatment with the current treatment plan in relation to the previous degrees of conformance based on the tracking of the current treatment, the current treatment plan and the provided previous conformance values.

Since a visualization is generated, which can be shown on a display to a physician performing the treatment and which is indicative of a current degree of conformance of the current treatment with the current treatment plan in relation to the previous degrees of conformance, the physician can see how well the current treatment conforms to the treatment plan in comparison to the degree of conformance achieved in previous treatments, thereby providing an assessment of the quality of the current treatment in relation to previous treatments.

The treatment plan providing unit can be a storing unit in which the current treatment plan is stored already and from which the current treatment plan can be retrieved for providing the same. However, the treatment plan providing unit can also be a receiving unit for receiving the current treatment plan from a treatment plan generating unit. The treatment plan providing unit can also be the treatment plan generating unit, i.e. the treatment plan providing unit can be adapted to generate the current treatment plan.

The previous conformance values can be values which result from a conformance measure applied to the respective previous treatments. These values resulting from applying the conformance measure can be regarded as being conformance measure values and can be, for instance, a) distances between positions of tracked interventional devices and planned positions of the interventional devices as defined by the previous treatment plans, b) a number or percentage of objectives, which were defined by the respective previous treatment plans and which were actually met by the respective previous treatments, c) values being indicative of deviations between a dose distribution defined by the respective previous treatment plans and actual dose distributions achieved by the previous treatments, et cetera. The previous conformance values can also be statistical values describing the population of these conformance measure values.

In an embodiment the treatment is performed by using an interventional device, wherein the tracking of the current treatment includes determining the position of the interventional device during the current treatment and wherein a) the treatment plan providing unit is adapted to provide the current treatment plan such that it includes a planned position of the interventional device, b) the conformance values providing unit is adapted to provide the previous conformance values such that they are indicative of previous degrees of conformance of positions of an interventional device determined during the previous treatments with planned positions included in the previous treatment plans, and c) the visualization unit is adapted to generate the visualization such that it is indicative of the current degree of conformance of the position determined during the current treatment with the planned position included in the current treatment plan in relation to the previous degrees of conformance based on the position determined during the current treatment, the planned position included in the current treatment plan and the provided previous conformance values. This visualization provides an assessment of the quality of the current position of the interventional device in relation to positions of interventional devices in previous treatments.

The interventional device can be a catheter like a brachytherapy catheter, a needle or another interventional device. The treatment is preferentially an interventional oncology treatment. The visualization unit is preferentially adapted to generate the visualization in real-time during the current treatment, in order to provide real-time guidance to the physician. Preferentially, the treatment assessment device also comprises an image providing unit for providing an image of the subject, wherein the visualization unit may generate the visualization such that the current degree of conformance is shown in relation to the previous degrees of conformance together with the image.

If the treatment requires a positioning of an interventional device like a brachytherapy catheter, it should be understood that preferentially the positioning of the interventional device is regarded as being a part of the treatment, i.e. the current treatment may be tracked by tracking the positioning of the interventional device, the previous conformance values can be indicative of previous degrees of conformance of previous positions of the interventional device with planned positions of the interventional device as defined by previous treatment plans, and the generated visualization can be indicative of a current degree of conformance of the current position of the interventional device with the planned position of the interventional device as defined by the current treatment plan in relation to the previous degrees of conformance.

The visualization unit can be adapted to provide a statistical value based on the provided previous conformance values and to use the statistical value for generating the visualization. The statistical value can statistically describe the population of previous conformance measure values, i.e. it may indicate a statistical property of this population, wherein this statistical property can be used for indicating the current degree of conformance in relation to the previous degrees of conformance in a relatively simple way. The previous conformance values can be conformance measure values, wherein the visualization unit can be adapted to determine a statistical value based on the previous conformance measure values. However, the previous conformance values can also already be statistical values, wherein the visualization unit can be adapted to provide these statistical values or to determine a further statistical value based on the provided statistical values.

In particular, the visualization unit can be adapted to provide the percentage of a) previous treatments conforming better or worse to the respective previous treatment plans than b) the current treatment conforms to the current treatment plan as the statistical value. Moreover, in an embodiment the visualization unit can be adapted to provide a range of acceptable degrees of conformance based on the statistical value and to visualize also the determined range of acceptable degrees of conformance, wherein the statistical value can be the standard deviation or another statistical value. Thus, while performing the treatment, for instance, while introducing a catheter or a needle into the subject, the current percentage of previous treatments conforming better or worse to the respective previous treatment plans than the current treatment conforms to the current treatment plan and/or the range of acceptable degrees of conformance can be visualized, wherein the physician can modify the current treatment, for instance, the physician can modify the current position of the catheter or the needle, such that the percentage of previous treatments conforming better or worse to the respective previous treatment plans than the current treatment conforms to the current treatment plan is improved and/or the current degree of conformance is within the range of acceptable degrees of conformance, respectively. This can allow for a further improved guidance of the physician during the treatment.

In a preferred embodiment the conformance values providing unit comprises a database including at least the previous conformance values, wherein the conformance values providing unit is adapted to provide the previous conformance values from the database, to determine a current conformance value based on the tracking of the current treatment and the current treatment plan and to update the database based on the current conformance value. In particular, the current conformance value may be added to the database for updating the same. For instance, the database can comprise distances between positions of interventional devices and corresponding planned positions as the previous conformance values, wherein a current distance between a current position of an interventional device and a planned position of the interventional device can be added to the database such that the current distance is used with the other conformance values in a following treatment.

The database preferentially includes previous conformance values being indicative of previous degrees of conformance of previous treatments, which have been performed by a same treatment system which is also used for performing the current treatment, with previous treatment plans. This allows the visualization unit to generate a visualization being indicative of the current degree of conformance of the current treatment with the current treatment plan in relation to the previous degrees of conformance achieved by the same treatment system. However, in other embodiments the current degree of conformance of the current treatment with the current treatment plan can also be indicated in relation to previous degrees of conformance achieved by other treatment systems within a same hospital or in another hospital. Hence, the database can include previous conformance values for different hospitals and/or different treatment systems having been used for performing the previous treatments and/or for different physicians having performed the previous treatments. This allows for a quality assessment of, for instance, different hospitals, different treatment systems and/or different physicians.

In an embodiment the treatment assessment device includes an outcome value determining unit for determining an outcome value being indicative of the outcome of the current treatment by using the database. The outcome value can be higher, if the outcome of the current treatment as defined by the current conformance value and optionally further parameters is better, and the outcome value can be smaller, if the outcome of the current treatment is expected to be lower. The database can comprise assignments between a) conformance values and possibly further parameters and b) outcome values, wherein based on the current conformance value and the possible further parameters and the assignments an outcome value can be determined for the current treatment. The further parameters used for determining the outcome value can be, for instance, a physician identification, a treatment system identification, an interventional device identification, a treatment protocol identification, the volume of an organ to be treated, et cetera.

In a further aspect of the present invention a treatment system for treating a subject is presented, wherein the treatment system comprises:

a treatment device for performing a treatment of the subject, a tracking unit for tracking the treatment, and a treatment assessment device as defined in claim 1 for assessing the treatment.

In another aspect of the present invention a treatment assessment method for assessing a treatment of a subject is presented, wherein a current treatment is tracked by a tracking unit and the treatment assessment method comprises:

providing a current treatment plan by a treatment plan providing unit, providing previous conformance values being indicative of previous degrees of conformance of previous treatments with previous treatment plans by a conformance values providing unit, and generating a visualization visualizing a current degree of conformance of the current treatment with the current treatment plan in relation to the previous degrees of conformance based on the tracking of the current treatment, the current treatment plan and the provided previous conformance values by a visualization unit.

In a further aspect of the present invention a computer program for assessing a treatment of a subject is presented, wherein the computer program comprises program code means for causing a treatment assessment device as defined in claim 1 to carry out the treatment assessment method as defined in claim 12, when the computer program is run on the treatment assessment device.

It shall be understood that the treatment assessment device of claim 1, the treatment system of claim 11, the treatment assessment method of claim 12 and the computer program of claim 13 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
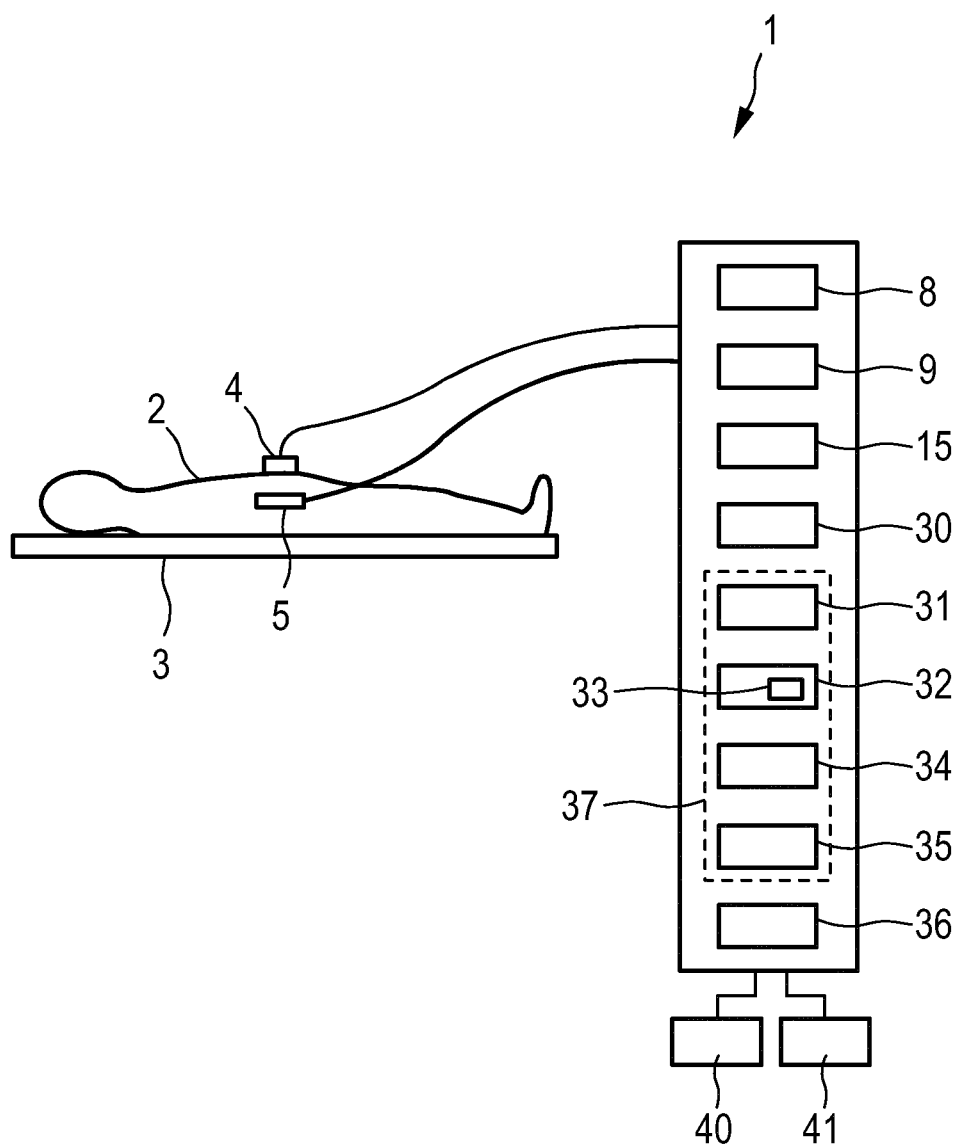
FIG. 1 shows schematically and exemplarily a treatment system for treating a subject.

FIG. 1 shows schematically and exemplarily a treatment system for treating a subject. In this embodiment the treatment system 1 is a brachytherapy system for applying a brachytherapy to subject 2 lying on a support means 3 like a table. The brachytherapy system 1 comprises a placing unit 5 for placing a radiation source close to or within a target region within the subject 2 for directing radiation emitted by the radiation source to the target region. The radiation source 10 is preferentially a radioactive radiation source emitting radioactive radiation like Ir-192. The placing unit 5 is exemplarily and schematically shown in more detail in FIG. 2.

The placing unit 5 comprises several elongated interventional devices 12, which in this embodiment are catheters, with tips 20 for being introduced into the subject 2. The placing unit 5 further comprises a drive wire 13 to which the radiation source 10 is attached, wherein the drive wire 13 with the radiation source 10 can be moved within each of the catheters 12 for placing the radiation source 10 at desired dwell positions for desired dwell times. The placing unit 5 further comprises a moving unit 14, which may also be regarded as being an afterloader and which is adapted to introduce the radiation source 10 into and to move the radiation source 10 within the different catheters 12 by using a motor. In particular, the moving unit 14 may be adapted to drive the radiation source 10 through an indexer that connects with the different catheters 12. For more details regarding this kind of placing the radiation source 10 within the subject reference is made to the document "A Practical Guide to Quality Control of Brachytherapy Equipment" edited by J. Venselaar and J. Perez-Calatayud, European Society for Therapeutic Radiology and Oncology (2004), which is herewith incorporated by reference.

The placing unit 5 can comprise further elements for assisting in placing the radiation source at the desired dwell positions for the desired dwell times within the subject 2. For instance, the placing unit can comprise a template which can be used for inserting the catheters 12 in a more uniform configuration into the subject 2.

Figure 3:
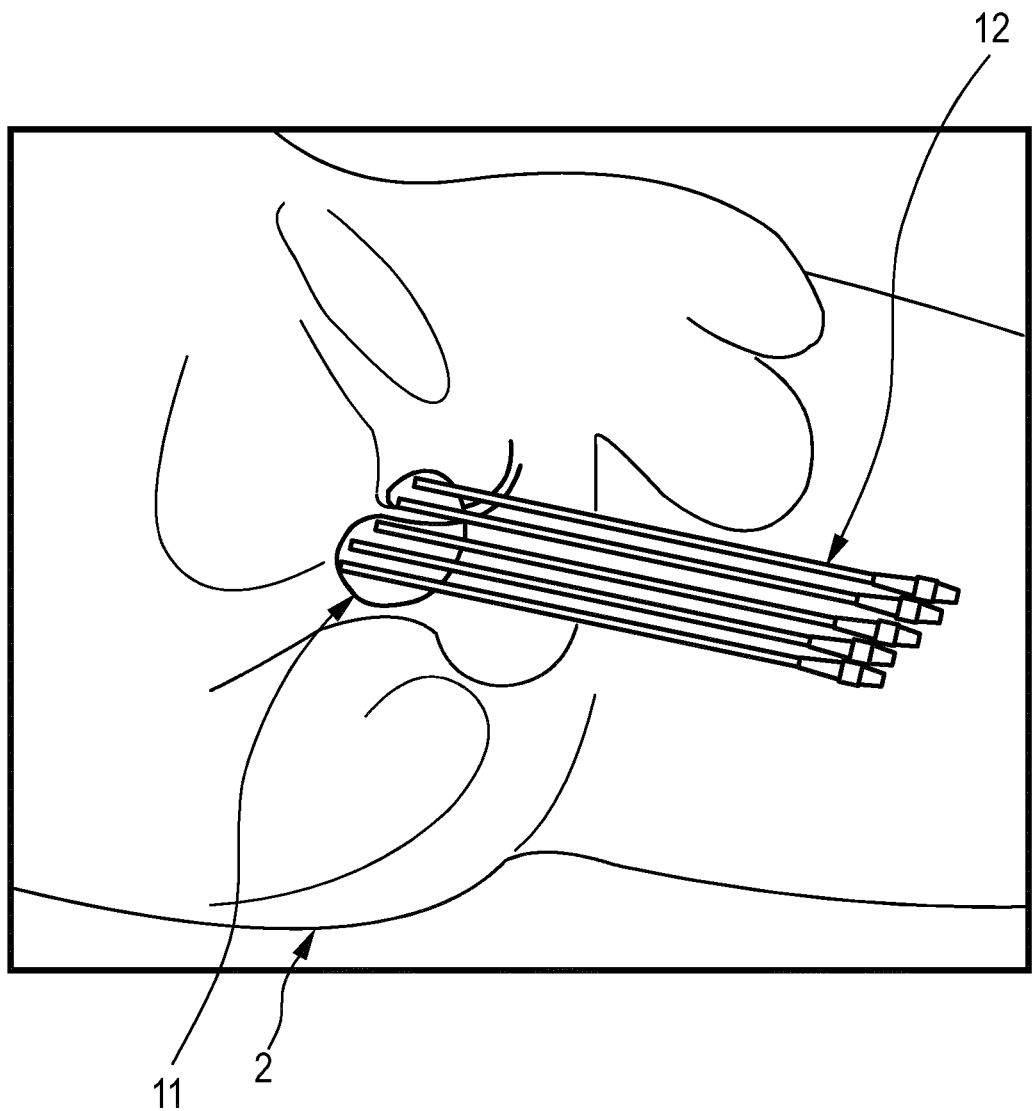
FIG. 3 illustrates schematically and exemplarily a possible arrangement of the brachytherapy catheters after having been introduced into the subject, FIGS. 4 to 6 schematically and exemplarily show a visualization being indicative of a current degree of conformance of a current treatment with a current treatment plan in relation to previous degrees of conformance.

In this embodiment the system 1 is adapted to treat a target region, which is preferentially a tumor region, in a prostate. The radiation source may be placed within the target region and/or close to the target region, i.e., in particular, adjacent to the target region. FIG. 3 shows schematically and exemplarily a possible arrangement of the catheters 12 of the placing unit 5 within the prostate 11.

Each catheter 12 comprises optical fibers with Bragg gratings, wherein an optical sensing control unit 15 may generate optical signals, which are indicative of the shape and hence the position of the respective catheter 12 within the subject 2, by using the optical fibers with the Bragg gratings. For more details regarding the determination of the shape and thus the position of the respective catheter 12 based on the optical signals reference is made to, for instance, the book "Fiber Optic Sensors" by F. T. S. Yu et al., Marcel Dekker Inc. (2002), especially chapter 4 of this book, which is herewith incorporated by reference. The determination of the shape and hence the position of the respective catheter 12 is determined by a position determination unit 30. The optical sensing control unit 15 and the position determination unit 30 can be regarded as forming a tracking unit for tracking the treatment by tracking the position of the respective catheter.

The system 1 further comprises an imaging unit 4, 8 being, in this embodiment, an ultrasound unit. The ultrasound unit comprises an ultrasound probe 4 and an ultrasound control unit 8. The ultrasound probe 4 may be placed on the outside surface of the subject 2 as schematically and exemplarily illustrated in FIG. 1, or the ultrasound probe may be arranged within the subject 2, in order to generate an image of the subject 2, especially of the target region. For instance, the ultrasound probe may be a transrectal ultrasound (TRUS) probe. The generated image can be shown to a user on a display 41, in order to guide the user while introducing the catheters 12 into the subject 2. In another embodiment the imaging unit can be another imaging modality like a magnetic resonance (MR) imaging modality.

A target region providing unit 9 can be adapted to determine the position of the target region within the subject 2 based on the image provided by the imaging unit 4, 8, for instance, by segmenting the target region within the provided image. The target region can be used by a treatment plan providing unit 31 for generating a treatment plan. The treatment plan can define planned positions of the catheters 12 and dwell positions and dwell times of the radiation source 10 within the catheters 12. The treatment plan providing unit 31 can be adapted to generate the treatment plan such that it defines dwell positions only in regions within or close to the target region. The treatment plan providing unit 31 can comprise treatment plan generation rules defining planned positions of the catheters 12 and dwell positions and dwell times of the radiation source 10 depending on the position of the target region.

The brachytherapy system 1 further comprises a conformance values providing unit 32 for proving conformance values being indicative of previous degrees of conformance of previous treatments with previous treatment plans. In this embodiment the conformance values providing unit 32 comprises a database 33 including at least the conformance values, wherein the conformance values are distances between a) positions of catheters determined during previous treatments and b) planned positions included in previous treatment plans. These conformance values indicate degrees of conformance of positions of the respective catheter determined during the previous treatments with planned positions included in the previous treatment plans.

The brachytherapy system further comprises a visualization unit 34 for generating a visualization being indicative of a current degree of conformance of the current treatment with the current treatment plan in relation to the previous degrees of conformance based on a) the tracking of the current treatment, i.e. in the present case the current position of the respective catheter 12 determined by optical shape sensing, b) the current treatment plan, i.e. in the present case the planned position of the respective catheter 12 as defined by the current treatment plan, and c) the provided previous conformance values. In this embodiment the visualization is indicative of the current degree of conformance of the position of the respective catheter 12 determined during the current treatment with the planned position included in the current treatment plan in relation to the previous degrees of conformance. The visualization is registered with the image of the subject 2 provided by the imaging unit 4, 8 and shown together with the image on the display 41.

Figure 4:
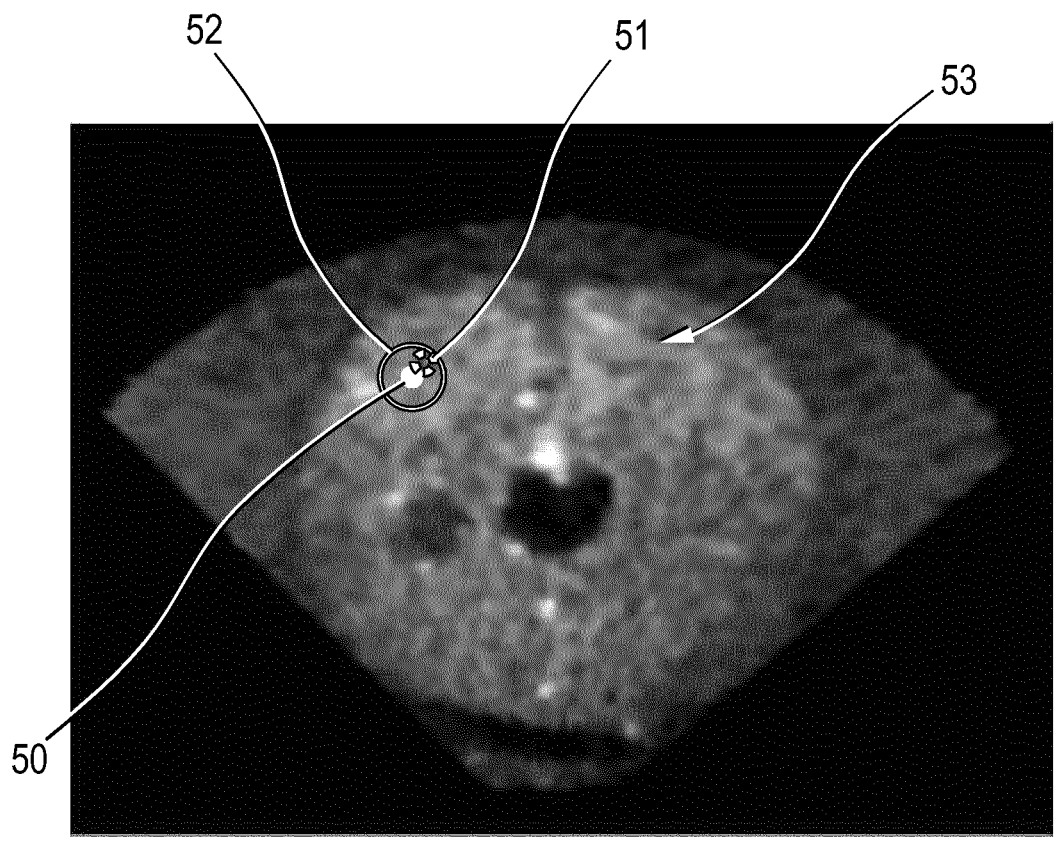

Preferentially, the visualization unit 34 is adapted to determine a statistical value based on the provided previous conformance values and to use the statistical value for generating the visualization. For instance, the visualization unit 34 can be adapted to determine a standard deviation based on the provided previous conformance values as a statistical value and to use the determined standard deviation for determining a range of acceptable degrees of conformance, i.e. in the present case, a range of acceptable distances between the planned position of the respective catheter 12 and the tracked current position of the respective catheter 12. The visualization of the determined range of acceptable degrees of conformance can be shown on the display 41 as illustrated in FIG. 4.

Figure 2:
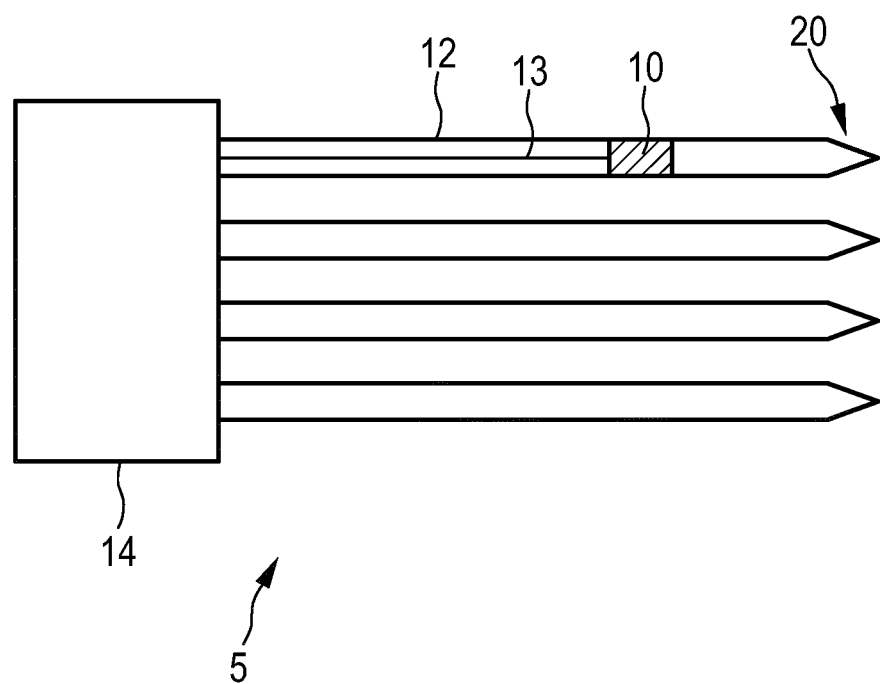
FIG. 2 shows schematically and exemplarily a placing unit comprising brachytherapy catheters of the treatment system.
Figure 5:
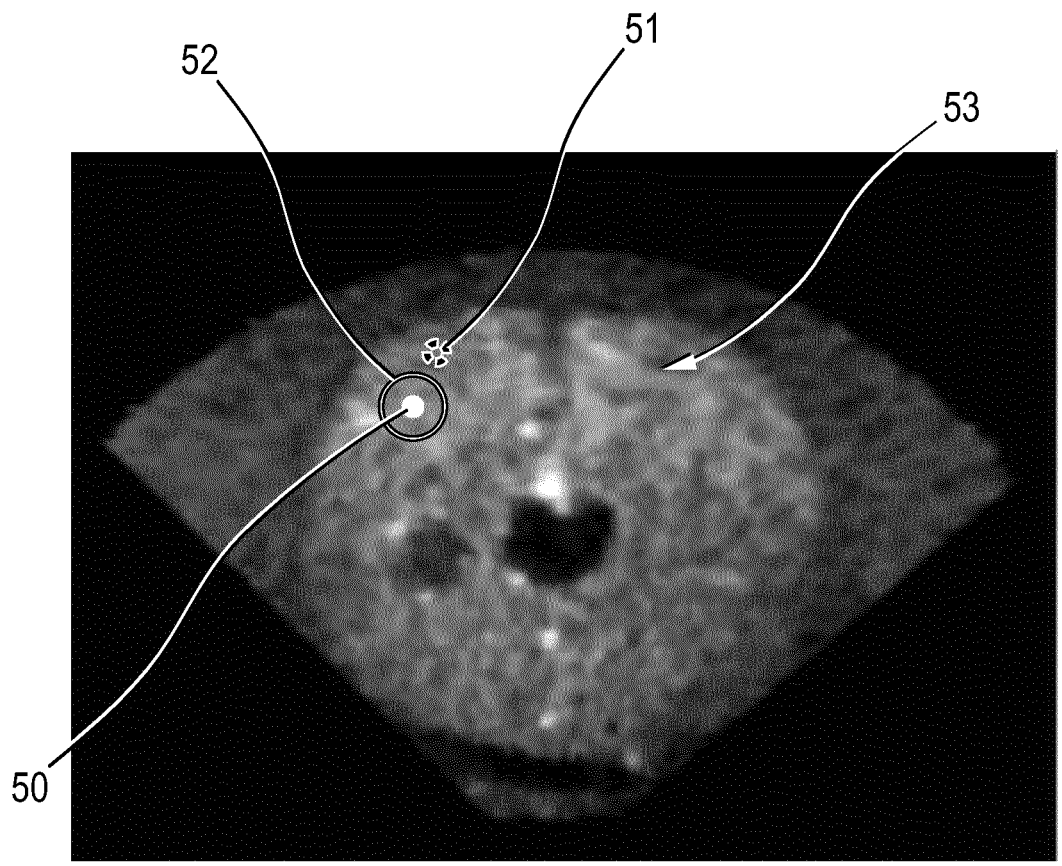

In this embodiment the catheters 12 are introduced into the subject 2 in a substantially parallel arrangement as illustrated, for instance, in FIG. 2. FIG. 4 shows a view of a plane being perpendicular to the parallel catheters 12, wherein in FIG. 2 only a tracked position 51 of a single catheter 12, which is currently positioned, and a corresponding planned position 50 are shown overlaid with an ultrasound image 53 of the subject. The circle 52 is used for indicating the determined range of acceptable degrees of conformance, i.e. tracked current positions of the respective catheter 12 within the circle 52 are regarded as being acceptable. The visualization unit 34 can be adapted to modify the appearance of the visualization depending on whether the tracked current position of the respective catheter 12 is within the range of acceptable degrees of conformance or not. For instance, the color of the tracked current position 51 shown on the display can depend on whether this position is within the determined range of acceptable degrees of conformance or not. In particular, in FIG. 4 the tracked current position of the respective catheter can be shown with a first color like green and in the situation illustrated in FIG. 5 the tracked current position 51 of the respective catheter 12 can be shown with a second color like red.

Figure 6:
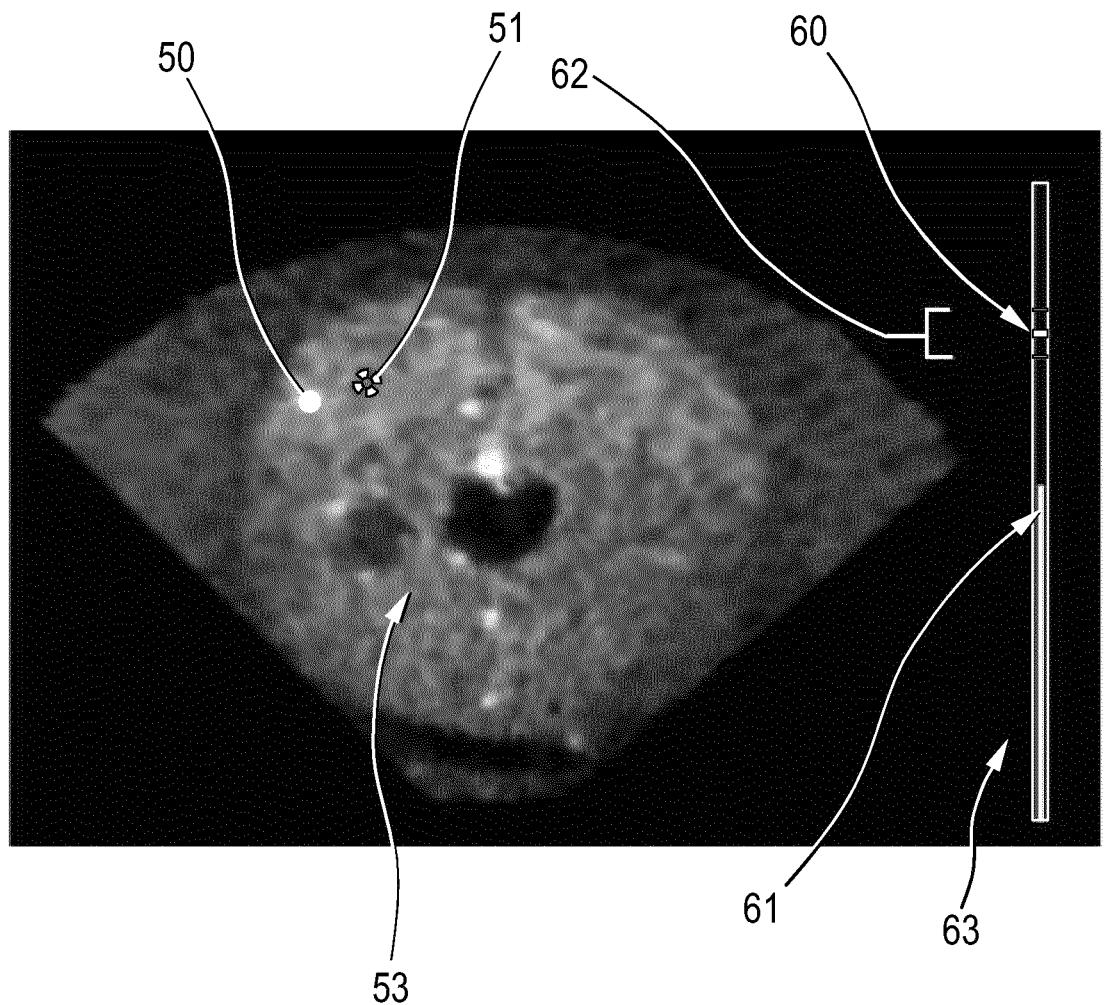
Figure 7:
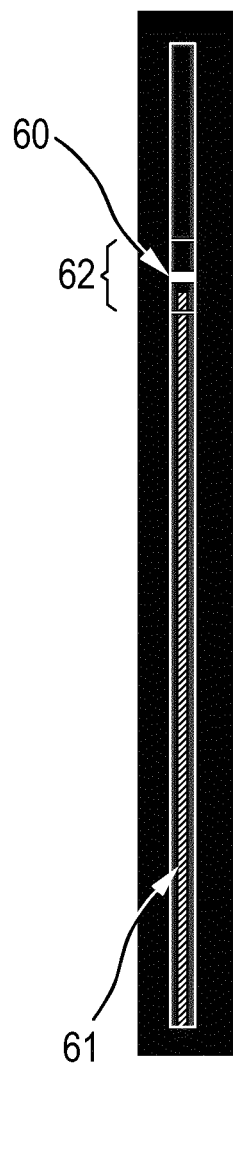
FIG. 7 shows schematically and exemplarily a graphical element of the visualization shown in FIG. 6 in a situation in which the degree of conformance of the current treatment with the current treatment plan in relation to the previous degrees of conformance is acceptable.
Figure 8:
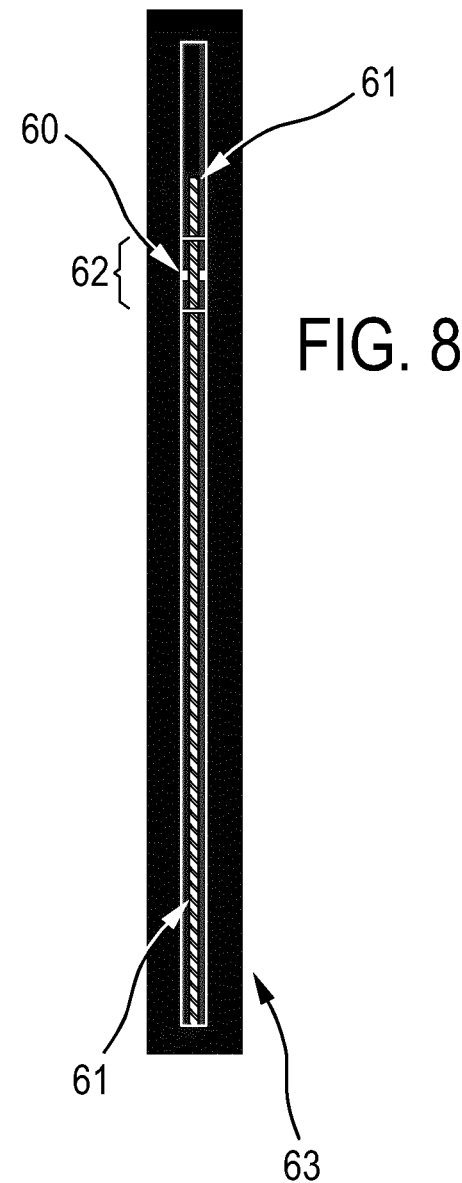
FIG. 8 shows schematically and exemplarily a graphical element of the visualization shown in FIG. 6 in a situation in which the degree of conformance of the current treatment with the current treatment plan in relation to the previous degrees of conformance is not acceptable.

FIG. 6 schematically and exemplarily shows another visualization being indicative of a current degree of conformance of the current treatment with the current treatment plan in relation to the previous degrees of conformance, which is generated based on the tracking of the current treatment, the current treatment plan and the provided previous conformance values, i.e. in this embodiment a visualization is shown, which is indicative of a current degree of conformance of the current position 51 of the respective catheter with the planned position of the respective catheter in relation to the previous degrees of conformance and which is generated based on the tracking of the current position of the respective catheter, the planned position of the respective catheter included in the current treatment plan and the provided previous deviations of the real catheter positions and the planned catheter positions in previous treatments. In this example the visualization comprises a graphical element 63 with a vertical bar 61 and a marker 60, wherein the distance between the upper end of the vertical bar 61 and the marker 60 illustrates the deviation between the current position of the catheter and the planned position. Also a range 62 of acceptable degrees of conformance, i.e. of acceptable deviations, is shown. FIG. 6 shows the graphical element 63 in a situation in which the physician tries to approach the planned position by moving the catheter towards the planned position. In this situation the bar 61 indicating the current position of the catheter may be shown with a first color. FIG. 7 shows the graphical element 63 in a situation in which the deviation between the planned position indicated by the marker 60 and the current position indicated by the bar 61 is acceptable, because the upper end of the bar 61 is within the margin 62. In this situation the bar 61 may be shown with a second color. FIG. 8 shows the graphical element 63 in a further situation in which the deviation between the current position of the catheter and the planned position has become too large, i.e. the deviation is not acceptable anymore and correspondingly the upper end of the bar 61 is not within the range 62 of acceptable degrees of conformance, i.e. of acceptable deviations. In this situation the bar 61 may be shown with a third color. In an embodiment the first color is white, the second color is green and the third color is red. However, in other embodiments other colors can of course be used. The range 62 of acceptable deviations is determined based on the previous deviations of previous treatments stored in the database 33. In particular, it may be or depend on the standard deviation of the previous deviations in the data base 33. By showing the range 62 the visualization indicates the current deviation in relation to previous deviations. Thus, a visual feedback can be provided, which uses a vertical bar with added color feedback to indicate the relation between the currently tracked position of the catheter in relation to acceptable deviations based on recorded statistics, wherein in this embodiment the bar turns green within the acceptable range and red when the acceptable range is exceeded.

Figure 9:
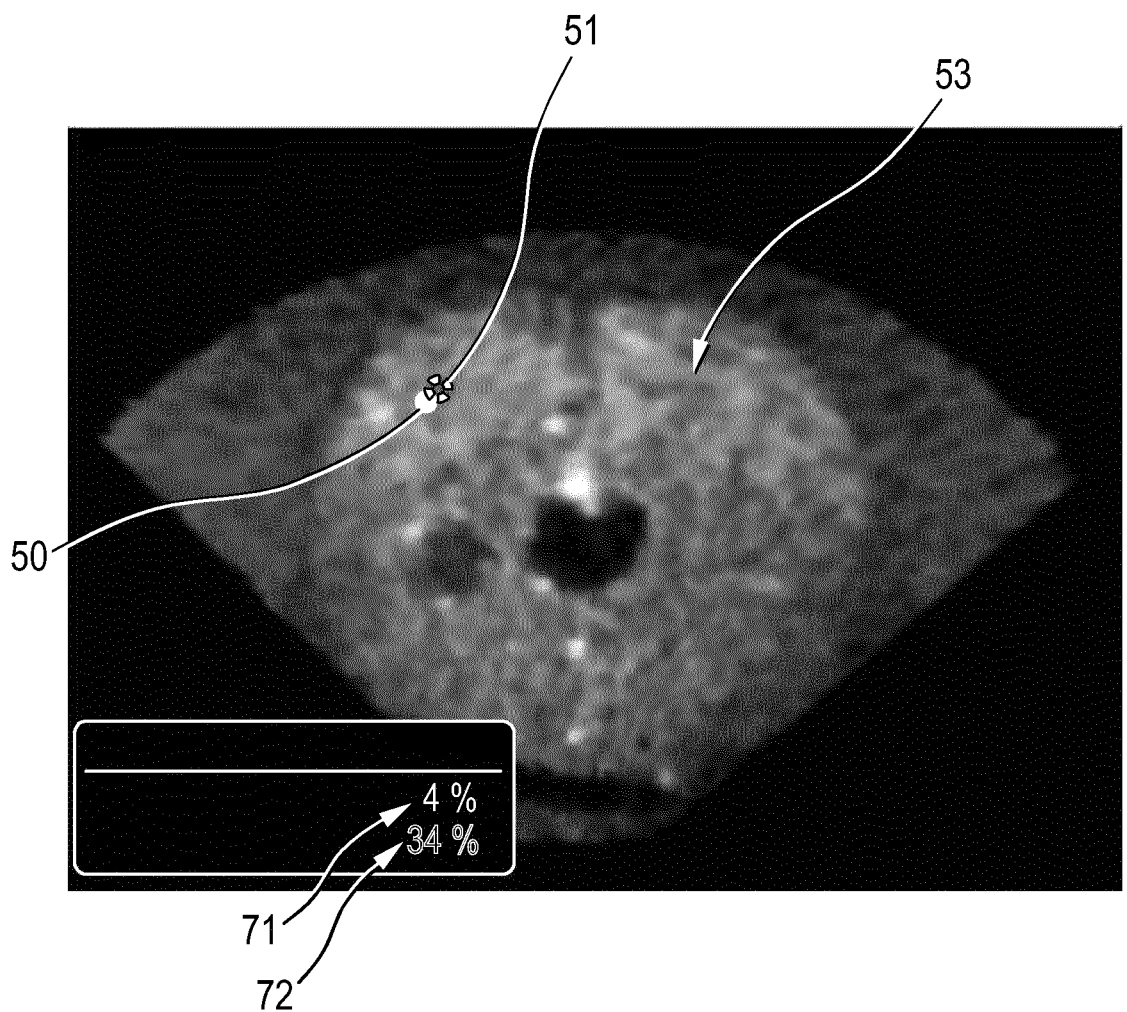
FIGS. 9 and 10 show schematically and exemplarily further visualizations being indicative of a current degree of conformance of a current treatment with a current treatment plan in relation to previous degrees of conformance.

FIG. 9 schematically and exemplarily shows a further possible visualization which can be generated by the visualization unit 34. In this example a percentage value 71 is shown, which indicates the percentage of previous treatments conforming better to the respective previous treatment plans than the current treatment conforms to the current treatment plan, wherein this percentage value only refers to the current catheter to be placed. A second percentage value 72 can refer to all catheters which have been placed already. If the respective percentage value is lower than a predefined threshold, the deviation is acceptable and this may be indicated by, for instance, showing the respective percentage value in a first color, wherein, if the respective percentage value is not smaller than the predefined threshold, this may be indicated by, for instance, showing the respective percentage value with another color. Thus, a percentile-based evaluation of the current catheter position can be offered to the user in real-time, in order to display the accuracy of the current catheter placement when compared to recorded statistics. In this example also a comparison of the total procedure accuracy conducted so far in relation to recorded statistics is displayed.

Figure 10:
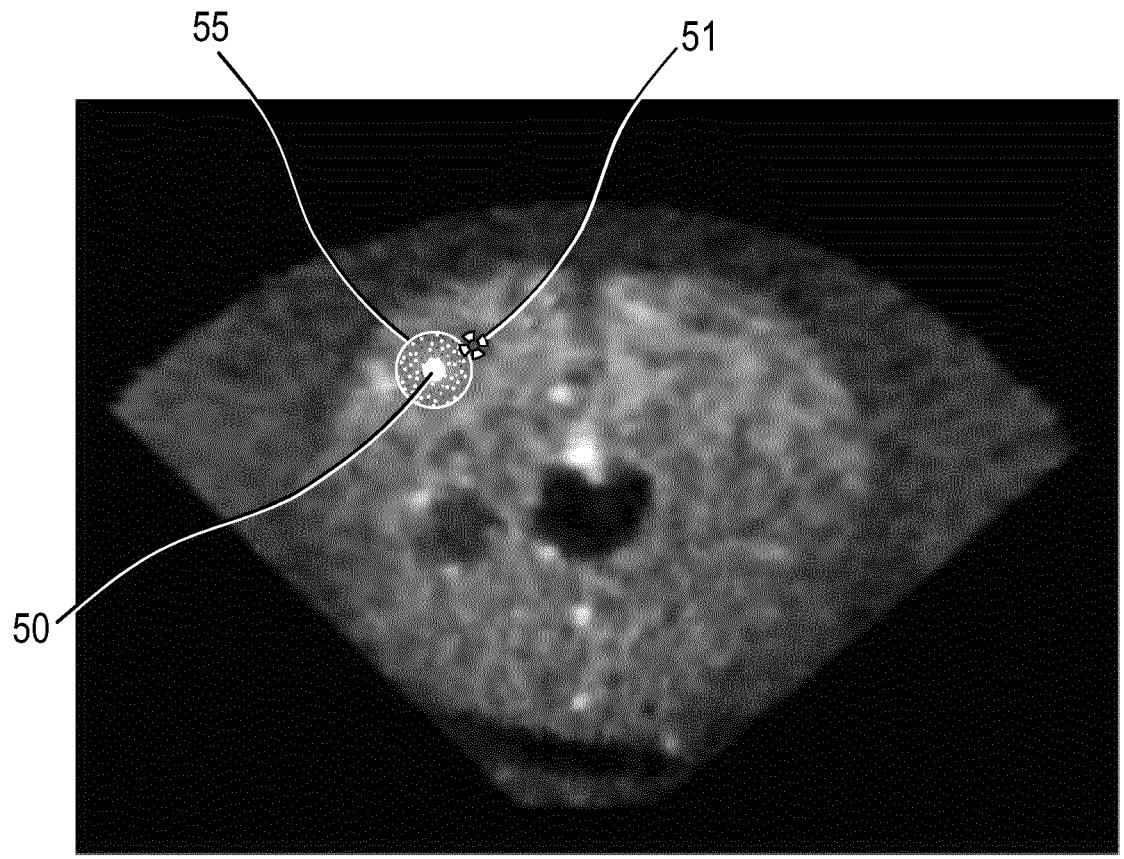

A further visualization which can be generated by the visualization unit 34 is exemplarily shown in FIG. 10. In this example previous deviations between tracked real catheter positions and planned catheter positions are indicated by a cloud 55 surrounding the planned position 50, wherein the density of the cloud increases with the number of previous deviations, i.e. if the current position 51 of the respective catheter is within a part of the cloud 55 being relatively dense, the current deviation is similar to many deviations in previous treatments. Thus, the deviation of the planned catheter position 50 in relation to its current position 51 combined with visual feedback of how this deviation relates to historically recorded deviations in catheter positioning can be shown by the visualization.

FIGS. 4 to 6, 9 and 10 show perpendicular views, i.e. an ultrasound image of a plane being perpendicular to the planned parallel catheter positions, wherein the tracked position and the planned position of the tip of the respective catheter are shown in this plane, i.e. projected in this plane. Alternatively or in addition, one or several views can be shown, which are oriented in another way. For instance, an ultrasound image can be shown, which is arranged in a plane being parallel to the planned catheter positions, wherein, while introducing the respective catheter, the planned position of the entire respective catheter or of only the tip of the respective catheter can be shown in this plane, i.e. can be projected into this plane. Also the tracked position of the respective entire catheter or of the tip of the respective catheter can be shown in this plane.

After a treatment has been performed, the deviations between the tracked positions of the brachytherapy catheters 12 and the corresponding planned positions can be added to the database 33, in order to use these deviations as previous deviations for subsequent treatments. In this embodiment the database 33 only includes deviations, i.e. conformance values, which relate to the same treatment system 1. However, in other embodiments the database can also include deviations measured with different treatment systems which may even be located in different hospitals. Thus, in the database the deviations may be stored for different hospitals and/or for different treatment systems which may be treatment systems of the same hospital or of different hospitals. The deviations may also be stored for different physicians having performed the treatments. This allows for a quality assessment depending on the respective hospital and/or the respective treatment system and/or the respective physician, i.e. it is possible to assess the quality of the respective hospital and/or of the respective treatment system and/or of the respective physician.

The treatment system 1 can further comprise an outcome value determining unit 35 for determining an outcome value being indicative of the outcome of the current treatment by using the database 33. Preferentially, for determining an outcome value in the database 33 not only the deviations are stored, but also further parameters characterizing the previous treatments and also the outcome of the previous treatments, wherein the outcome can be indicated by the outcome value. A higher outcome value may indicate a better outcome and a lower outcome value may indicate a worse outcome. The database 33 can comprise assignments between parameters characterizing the previous treatments and outcome values, wherein these assignments can be used together with corresponding parameters of the current treatment for determining an outcome value for the current treatment. Also the outcome value may be shown on the display 41. The parameters of the current treatment may be input into the treatment system by using an input unit 40 like a keyboard, a computer mouse, a touch pad, et cetera. The outcome value may be determined in real-time while entering parameters characterizing the current treatment and/or while moving the respective brachytherapy catheter within the subject 2 and shown on the display 41, in order to allow the physician to improve the possible outcome by modifying the parameters and/or the current deviation of the position of the respective brachytherapy catheter from the respective planned position.

The treatment system 1 further comprises a brachytherapy control unit 37 for controlling the moving unit 14 depending on the dwell positions and dwell times defined by the treatment plan.

The treatment plan generation unit 31, the conformance values providing unit 32, the visualization unit 34 and the outcome value determining unit 35 can be regarded as being units of a treatment assessment device 37.

Figure 11:
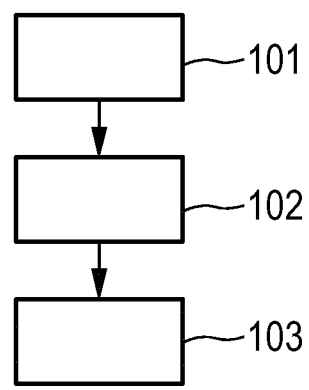
FIG. 11 shows a flowchart exemplarily illustrating an embodiment of a treatment method for treating a subject.

In the following an embodiment of a treatment method for treating a subject will exemplarily be described with reference to a flowchart shown in FIG. 11.

In step 101 the treatment plan providing unit 31 provides a current treatment plan defining positions of the brachytherapy catheters 12 within the subject, dwell positions within the brachytherapy catheters 12 and dwell times. In step 102 the position of a brachytherapy catheter 12 is tracked while being introduced into the subject 2 by a physician, previous conformance values being indicative of previous degrees of conformance of previous treatments with previous treatment plans are provided by the conformance values providing unit 32 and a visualization is generated by the visualization unit 34 based on the tracking of the current treatment, i.e. in this embodiment the tracking of the position of the respective brachytherapy catheters 12, the current treatment plan and the provided previous conformance values, wherein the visualization is indicative of a current degree of conformance of the current treatment with the current treatment plan in relation to the previous degrees of conformance. In particular, the visualization unit 34 is adapted to visualize a current deviation of a position of a brachytherapy catheter from a planned position in relation to previous deviations between tracked positions of brachytherapy catheters and corresponding planned positions based on the tracking of the current position of the respective brachytherapy catheter, the provided current treatment plan and the previous deviations of tracked positions of brachytherapy catheters from corresponding planned positions of previous treatments stored in the database 33. The generated visualization is shown on the display 41.

After in step 102 all brachytherapy catheters 12 have been placed within the subject 2, in step 103 the brachytherapy control unit 37 controls the movement of the radiation source 10 within the brachytherapy catheters 12 in accordance with the treatment plan.

The part of the treatment method performed in step 102 can be regarded as forming a treatment assessment method for assessing a treatment of a subject.

In focal therapy interventional devices like needles and possibly other instruments are positioned inside or close to, for instance, a tumor to deliver a therapeutic dose of an ablative energy. The focal therapy is, for example, brachytherapy, cryotherapy, a thermal ablation therapy, et cetera. The focal therapy can be carried out by an image-guided interventional system, which can also be regarded as being an image-guided treatment system, wherein the positioning of the interventional device and the possible further instruments can be supported by integrating navigation technologies like electromagnetic tracking in the interventional device and the possible further instruments. The tracked position of the respective device or instrument can then be shown on a display in combination with a real-time image of the target which might be a tumor. Also, a distance between the current position of the respective device or instrument and a target can be shown on the display by using a corresponding graphical element. This guidance assistance can be extended by presenting a difference between planned parameters defined by a treatment plan and corresponding parameters which may be derived from the positioning of the respective device or instrument. For example, in brachytherapy a difference between a planned dose as defined by the treatment plan and a delivered dose derived from the current position of one or several brachytherapy catheters can be determined and presented on the display, in order to assess the degree of conformance of the current treatment with the treatment plan and in order to show the result of this assessment. This guidance assistance provides real-time information on device or instrument positioning and on plan conformance during the respective treatment procedure. This guidance assistance can be improved by using the treatment system and method described above with reference to FIGS. 1 to 11, especially by providing insights into the quality of positioning the respective device or instrument and about the degree of plan conformance in relation to other procedures and optionally also in relation to procedure outcome. It is especially possible to assess how well the respective physician is doing compared to previous interventions, i.e. previous treatments, or interventions carried out by other physicians. This can give the physician an indication how accurate, for instance, needles or catheters need to be placed and optionally how current deviations relate to treatment outcome.

The treatment system and method described above with reference to FIGS. 1 to 11 allows for real-time guidance and quality assurance, wherein during a treatment data can be collected in real-time and compared with previous conformance values stored in the database, which were collected in other procedures, particularly in other hospitals, using similar treatment systems, i.e. using treatment systems of the same type. Also the collected data can be stored in the database, in order to enable later quality assurance in the respective hospital. These data can also be shared with a central service to allow for comparisons between different hospitals.

The treatment system and method described above with reference to FIGS. 1 to 11 can be adapted to perform a brachytherapy by using, for instance, 5 to 15 brachytherapy catheters to be placed in or near a lesion in the prostate. The plan conformance, i.e. the degree or conformance of a current treatment with a current treatment plan, can be measured, for instance, by measuring the distances between the planned catheter positions and the corresponding tracked real positions of the catheters. When positioning a respective catheter within the prostate, the respective distance between the tracked current position of the catheter and the corresponding planned position can be measured in real-time and be shown on the display, in order to guide the physician. The treatment system and method described above with reference to FIGS. 1 to 11 extend this guidance by a statistically motivated guidance, for example, by guiding the physician based on the percentage of catheters that were placed in previous procedures closer or further away than the current catheter. In order to provide this statistically motivated guidance, the number and covariances of previous samples, i.e. of previous treatments, may be used. This information can be stored in the database and the database can be updated by updating the number and covariances based on the distances measured during the current treatment. This statistical feedback loop can be used locally, in order to provide a measure for the placement accuracy for the current interventional system, i.e. for the current treatment system. The data stored in the database can also be exchanged with similar systems in the hospital, in order to allow for a quality assurance of all treatments, for instance, of all focal HDR brachytherapy procedures, performed in the respective hospital.

In an embodiment the previous conformance values stored in the database are statistical values describing the population of the previous distances between a) positions of catheters determined during previous treatments and b) planned positions included in previous treatment plans. The visualization unit can then be adapted to determine the variance and hence the standard deviation based on these statistical values and to determine a range of acceptable degrees of conformance based on the determined standard deviation. The statistical values stored in the database, which can be used for determining the variance and hence the standard deviation, can be the mean and the sum of squared distances between a) positions of catheters determined during previous treatments and b) planned positions included in previous treatment plans. This database can be updated by updating the stored mean by using the current distance between a) a current position of a respective catheter determined during a current treatment and b) a planned position included in a current treatment plan. Also the stored sum of squared differences can be updated by using the current distance. In higher dimensional cases the sum of differences to be maintained for cross terms are covariances.

Although in above described embodiments the conformance values are distances between a) positions of catheters determined during previous treatments and b) planned positions included in previous treatment plans or statistical values describing a population of these distances, in other embodiments the conformance values can also be other values being indicative of other kinds of degrees of conformance of previous treatments with previous treatment plans. For instance, the conformance values can be indicative of a degree of dose conformance of treatments with treatment plans. In particular, the previous conformance values can be indicative of degrees of conformance of previous dose distributions, which had been achieved in previous treatments, with dose distributions to be achieved by the respective previous treatment plans. The previous conformance values can also be indicative of previous degrees of conformance of previous treatments with objectives defined by previous treatment plans. For instance, the previous conformance values can be indicative of the number or percentage of objectives, which have been defined by the respective previous treatment plans and which have been achieved by the respective actual previous treatments. A first objective defined by a treatment plan could be that more than 95 percent of a target region should receive 100 percent of a prescribed dose and a second objective also defined by the treatment plan could be that, for instance, the volume of the bladder and rectum receiving 75 percent of a prescription dose should be kept to less than 1 cm$^3$. These previous conformance values and possibly further parameters like a treatment time, a volume of a target region to be treated, et cetera can be stored in the database. Thus, also these conformance values and possible further parameters can be used in a statistical feedback loop, wherein a quality assessment can be performed with respect to these data. For instance, the dose conformance or the percentage of met objectives, which may be regarded as being a protocol conformance, of different hospitals and/or of different physicians and/or of different treatment systems can be compared for assessing the same.

In an embodiment a penalty function can be used for providing conformance values being indicative of degrees of conformance of treatments with objectives defined in respective treatment plans. The penalty function can be or depend on a summation of penalty terms which refer to respective objectives, wherein the respective penalty term can provide a higher value, if the respective objective is less well met. For instance, a first objective could be delivering more than a certain amount of dose to a target and a second objective could be not delivering more than another amount of dose to an organ at risk. This could be penalized by using a summation of two penalty terms, being the percentage of the target not receiving enough dose and the percentage of the organ at risk receiving too much dose. This example is a simple linear penalty function. However, the dependence can also be different. For instance, all terms can be made quadratically or higher dimensional. In an embodiment a penalty function might be used, which is known to be considered in inverse, automatic planning algorithms for planning a treatment in which, for instance, a radiation dose is applied to a patient.

The current treatment is tracked, in order to allow for a comparison of the current treatment with the current treatment plan. The tracking unit is therefore adapted to track at least an aspect of the treatment, which should be used for performing this comparison. For instance, if the position of an interventional device should be compared with a planned position of the interventional device, the tracking unit is adapted to track at least the position of the interventional device, in order to track the treatment. If the current dose distribution should be compared with a planned dose distribution, the tracking unit can be adapted to track at least the current dose distribution. This might be done directly or indirectly by tracking the position of the radiation source applying the dose and by calculating the current dose distribution based on the tracked position and the characteristics of the radiation provided by the radiation source. The tracking unit may also be adapted to track how many objectives defined by the treatment plan have been achieved. In particular, the tracking unit may be adapted to track the position of the radiation source applying the dose, to calculate which parts of the patient have received how much dose and to determine whether the calculation result corresponds to objectives which are given by the treatment plan and which define which part of the patient should receive how much dose.

The parameters stored in the database can be scalar parameters, but they can also be parameters of another kind like normalized vectors. For instance, dose volume histograms of particulars organs can be stored in the database. In particular, planned volume dose histograms and actually obtained dose volume histograms can be stored in the database for different treatments. The parameters can be stored for different covariates like an identification of a respective physician having performed the respective treatment, an identification of a type of the treatment system or of a part of a treatment system used for performing the respective treatment, for instance, of one or several imaging devices used by the treatment system for assessing the impact of different imaging devices, an identification of the respective treatment system or of a part of the respective treatment system, for instance, of tracking sensors of the respective treatment system for monitoring the quality of these tracking sensors, an identification of a treatment protocol used for the respective treatment, in order to monitor the treatment outcome for different protocols, the volume of one or more organs of the subject treated by the respective treatment procedure, in order to, for instance, monitor if certain anatomical differences are less suitable for particular forms of therapy, et cetera. Also further data can be stored in the database like the date of the respective treatment, in order to, for instance, enable trend monitoring on, for example, running averages. Also treatment costs can be stored in the database.

The data in the database can also be stored together with patient data such that the stored data can be related to the treatment outcome during follow up. The outcome may refer to the efficacy of the treatment as well as the occurrence of treatment side effects.

Figure 12:
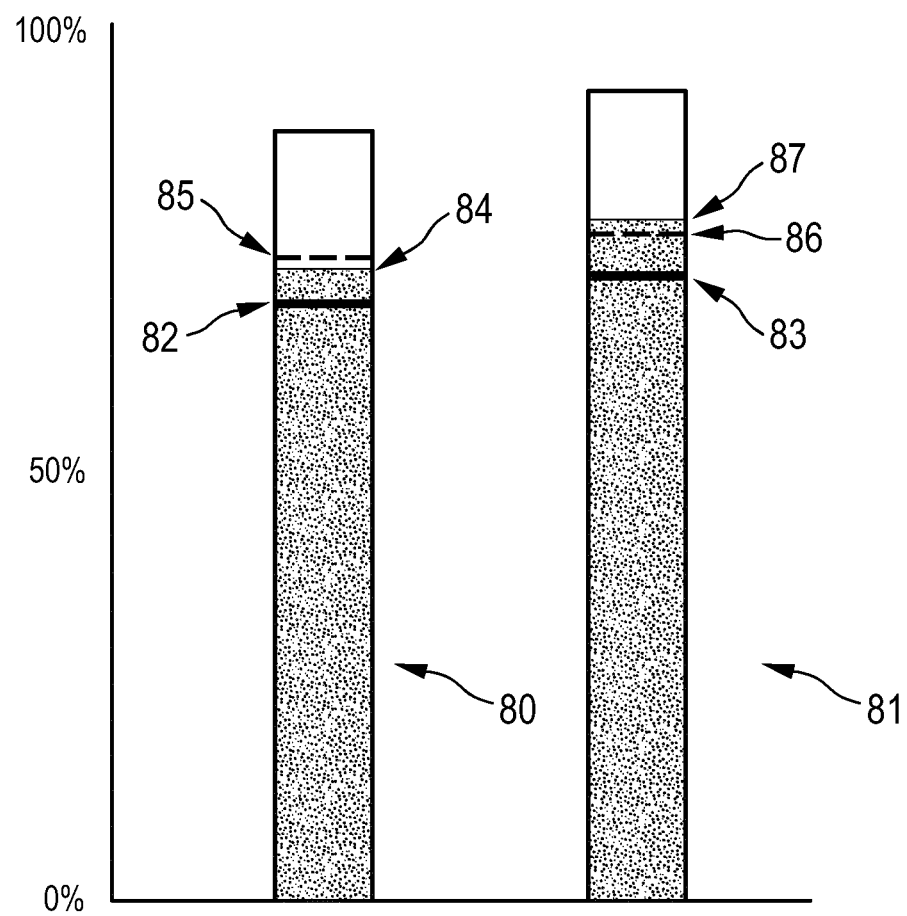
FIG. 12 illustrates schematically and exemplarily a possible result of a quality assurance procedure which is based on data determined during treatments.

FIG. 12 schematically and exemplarily illustrates the quality of a last treatment in comparison to previous treatments. In this example two bars 80, 81 are shown, wherein a first bar 80 refers to the dose conformance and a second bar 81 refers to the protocol conformance. The length of the respective bar 80, 81 indicates the best values stored in the data base, wherein the lines 82, 83 indicate acceptable degrees of conformance, i.e. degrees of dose conformance and degrees of protocol conformance above the lines 82, 83 are acceptable. The broken lines 85, 86 indicate average degrees of conformance and the lines 84, 87 indicate the degrees of conformance of the last treatment.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or devices may fulfill the functions of several items recited in the claims. The mere fact that certain measures are recited in mutually different dependent claims does not indicate that a combination of these measures cannot be used to advantage.

Procedures like the determination of a treatment plan, the determination of conformance values, the generation of a visualization, et cetera performed by one or several units or devices can be performed by any other number unit or devices. These procedures and/or the control of the treatment assessment device in accordance with the treatment assessment method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a treatment assessment device for assessing a treatment of a subject, wherein a current treatment is tracked by a tracking unit and previous conformance values being indicative of previous degrees of conformance of previous treatments with previous treatment plans are provided. A visualization unit generates a visualization being indicative of a current degree of conformance of the current treatment with the current treatment plan in relation to the previous degrees of conformance based on the tracking of the current treatment, the current treatment plan and the provided previous conformance values. The visualization can be shown on a display such that a physician can see how well the current treatment conforms to the treatment plan in comparison to the degree of conformance achieved in previous treatments, thereby providing an assessment of the quality of the current treatment in relation to previous treatments.

The invention claimed is:

1. A treatment assessment device for assessing a treatment of a subject, wherein a current treatment is tracked by a tracking unit and the treatment assessment device comprises:
   a treatment plan providing unit for providing a current treatment plan,
   a conformance values providing unit for providing previous conformance values being indicative of previous degrees of conformance of previous treatments with previous treatment plans, and
   a visualization unit for generating a visualization being indicative of a current degree of conformance of the current treatment with the current treatment plan in relation to the previous degrees of conformance based on the tracking of the current treatment, the current treatment plan and the provided previous conformance values.

2. The treatment assessment device as defined in claim 1, wherein the treatment is performed by using an interventional device, wherein the tracking of the current treatment includes determining the position of the interventional device during the current treatment and wherein:
   the treatment plan providing unit is adapted to provide the current treatment plan such that it includes a planned position of the interventional device,
   the conformance values providing unit is adapted to provide the previous conformance values such that they are indicative of previous degrees of conformance of positions of an interventional device determined during the previous treatments with planned positions included in the previous treatment plans,
   the visualization unit is adapted to generate the visualization such that it is indicative of the current degree of conformance of the position determined during the current treatment with the planned position included in the current treatment plan in relation to the previous degrees of conformance based on the position determined during the current treatment, the planned position included in the current treatment plan and the provided previous conformance values.

3. The treatment assessment device as defined in claim 1, wherein the visualization unit is adapted to provide a statistical value based on the provided previous conformance values and to use the statistical value for generating the visualization.

4. The treatment assessment device as defined in claim 3, wherein the visualization unit is adapted to provide the percentage of a) previous treatments conforming better or worse to the respective previous treatment plans than b) the current treatment conforms to the current treatment plan as the statistical value.

5. The treatment assessment device as defined in claim 3, wherein the visualization unit is adapted to determine a range of acceptable degrees of conformance based on the statistical value and to visualize also the determined range of acceptable degrees of conformance.

6. The treatment assessment device as defined in claim 5, wherein the visualization unit is adapted to provide a standard deviation based on the provided previous conformance values as the statistical value.

7. The treatment assessment device as defined in claim 1, wherein the conformance values providing unit comprises a database including at least the conformance values, wherein the conformance values providing unit is adapted to provide the conformance values from the database, to determine a current conformance value based on the tracking of the current treatment and the current treatment plan and to update the database based on the current conformance value.

8. The treatment assessment device as defined in claim 7, wherein the database includes conformance values being indicative of previous degrees of conformance of previous treatments, which have been performed by a same treatment system which is also used for performing the current treatment, with previous treatment plans.

9. The treatment assessment device as defined in claim 7, wherein the database includes the conformance values for different hospitals and/or different treatment systems having been used for performing the previous treatments and/or for different physicians having performed the previous treatments.

10. The treatment assessment device as defined in claim 7, wherein the treatment assessment device includes an outcome value determining unit for determining an outcome value being indicative of the outcome of the current treatment by using the database.

11. A treatment system for treating a subject, wherein the treatment system comprises:
- a treatment device for performing a treatment of the subject,
- a tracking unit for tracking the treatment, and
- a treatment assessment device as defined in claim 1 for assessing the treatment.

12. A computer program for assessing a treatment of a subject, the computer program comprising program code means for causing a treatment assessment device as defined in claim 1 to carry out, when the program is run on the treatment device, a treatment assessment method comprising:
- providing a current treatment plan by a treatment plan providing unit,
- providing previous conformance values being indicative of previous degrees of conformance of previous treatments with previous treatment plans by a conformance values providing unit, and
- generating a visualization visualizing a current degree of conformance of the current treatment with the current treatment plan in relation to the previous degrees of conformance based on the tracking of the current treatment, the current treatment plan and the provided previous conformance values by visualization unit.

* * * * *